United States Patent [19]

Sonoyama et al.

[11] Patent Number: 4,696,897
[45] Date of Patent: Sep. 29, 1987

[54] PROCESS FOR PREPARING 2-KETO-L-GULONIC ACID

[75] Inventors: Takayasu Sonoyama; Shigeo Yagi; Bunji Kageyama, all of Osaka, Japan

[73] Assignee: Shionogi & Co., Ltd., Osaka, Japan

[21] Appl. No.: 747,393

[22] Filed: Jun. 21, 1985

Related U.S. Application Data

[63] Continuation of Ser. No. 469,781, Feb. 25, 1983, abandoned.

[30] Foreign Application Priority Data

Mar. 5, 1982 [JP] Japan .................................. 57-35455

[51] Int. Cl.$^4$ .......................... C12P 39/00; C12P 7/60
[52] U.S. Cl. ........................................ 435/42; 435/138.
[58] Field of Search .................................. 435/42, 138

[56] References Cited

U.S. PATENT DOCUMENTS 3,998,697  12/1976  Sonoyama ........................... 435/138

OTHER PUBLICATIONS

"Identification Methods for Microbiologists", B. M. Gibbs et al., eds., Part B, Chapt. entitled Methods for Identifying Acetic Acid Bacteria, by J. G. Carr, pp. 1–8, Academic Press, New York, 1968.
Wakisaka, "Agr. Biol. Chem.", vol. 28, No. 6, pp. 369–374, (1964).
Wakisaka, "Agr. Biol. Chem.", vol. 28, No. 12, pp. 819–827, (1964).
Breed et al., "Bergey's Manual of Determinative Bacteriology", 7th Ed., pp. 182–189; 349–359, (1957).
Bergey's Manual of Determinative Bacteriology", 8th Ed., pp. 251–253, 332–339.
Sonoyama, T. et al., Applied and Environmental Microbiology, vol. 43, No. 5, 1064–1069, (1982).

Primary Examiner—Sidney Marantz
Attorney, Agent, or Firm—Birch, Stewart, Kolasch & Birch

[57] ABSTRACT

2-Keto-L-gulonic acid is prepared directly from D-glucose by microbial conversion utilizing mixed culturing on a medium containing D-glucose, employing two kinds of microorganisms; the first, a 2,5-diketo-D-gluconic acid producing microorganism which belongs to genus Erwinia and the second, a 2-keto-L-gulonic acid producing microorganism which belongs to genus Brevibacterium or Corynebacterium. The incubation of the microorganisms in a medium containing D-glucose is used in the disclosed process. By-production of 2-keto-D-gluconic acid, the undesired isomer of the intended product is effectively prevented by employing mixed culturing because of the co-existence of both microorganisms in the medium during at least part of the entire cultivation. Namely, 2-keto-D-gluconic acid produced by the second microorganism is utilized by the first microorganism to produce 2,5-diketo-D-gluconic acid which is subsequently converted into 2-keto-L-gulonic acid by the second microorganism.

20 Claims, No Drawings

PROCESS FOR PREPARING 2-KETO-L-GULONIC ACID

This application is a continuation of application Ser. No. 469,781, filed on Feb. 25, 1983, now abandoned.

BACKGROUNDS AND FIELD OF THE INVENTION

The present invention relates to a microbial production process wherein 2-keto-L-gulonic acid is obtained directly from D-glucose by a mixed culture of two kinds of microorganisms in a single fermenter to allow them to produce and accumulate 2-keto-L-gulonic acid which is then recovered from the fermenter.

DESCRIPTION OF THE PRIOR ART

The present inventors, who had been engaged in the study on the microbial production of 2-keto-L-gulonic acid, have previously found various microorganisms capable of producing 2-keto-L-gulonic acid from 2,5-diketo-D-gluconic acid and invented processes for preparing 2-keto-L-gulonic acid or salt thereof by a microbial conversion of 2,5-diketo-D-gluconic acid which is obtained by oxidative fermentation of D-glucose (See, for instance, U.S. Pat. Nos. 3,922,194(R. 30,872), 3,959,076 and 3,963,574).

It is well known that 2,5-diketo-D-gluconic acid, the precursor of 2-keto-L-gulonic acid in the processes of these inventions, is obtainable from D-glucose in a high yield by the oxidative activity of microorganisms which belong to the genus Gluconobacter (according to the definition given in Bergey's Manual of Determinative Bacteriology 8th Ed., and the genus Gluconobacter therefore includes genera Acetobacter, Acetomonas and Gluconobacter described in Bergey's Manual of Determinative Bacteriology 7th Ed.). On the other hand, the present inventors have recently found that several microorganisms which belong to genus Erwinia can effectively produce 2,5-diketo-D-Gluconic acid from D-glucose in a high yield (See, for instance, European Patent Publication No. 0 046 284).

Apart from this, the present inventors had previously found the following facts (See, for instance, U.S. Pat. No. 3,998,697). (a) Even if both of 2,5-diketo-D-gluconic acid-producing microorganism and 2-keto-L-gulonic acid-producing microorganism are allowed to be present together in a fermentation medium, the 2,5-diketo-D-gluconic acid produced by the 2,5-diketo-D-gluconic acid-producing strain can be smoothly converted into 2-keto-L-gulonic acid without any difficulty. (b) When the 2,5-diketo-D-gluconic acid producing microorganism and 2-keto-L-gulonic acid producing microorganism are present together in a cultured medium, an undesired optical isomer, 2-keto-D-gluconic acid which is otherwise produced by the 2-keto-L-gulonic acid-producing microorganism is not accumulated in the cultured medium. (c) The main reason for the absence of accumulation of 2-keto-D-gluconic acid in the cultured medium is that the 2-keto-D-gluconic acid once produced by the 2-keto-L-gulonic acid-producing strain is converted again into 2,5-diketo-D-gluconic acid by the 2,5-diketo-D-gluconic acid-producing microorganism and the 2,5-diketo-D-gluconic acid is then converted into 2-keto-L-gulonic acid.

In the previously-described invention (U.S. Pat. No. 3,998,697), the present inventors have disclosed that a microorganism which belongs to genus Gluconobacter can be used as the 2,5-diketo-D-gluconic acid producing microorganism while a microorganism which belongs to genus Brevibacterium or Corynebacterium can be used as the 2-keto-L-gulonic acid-producing microorganism, and the concomitant production of 2-keto-D-gluconic acid can be eliminated by the combined use of both microorganisms.

However, the effect of combination and compatibility of a microorganism which belongs to genus Erwinia with one which belongs to genus Brevibacterium or Corynebacterium has not yet been established.

SUMMARY OF THE INVENTION

It is therefore an object of the present invention to provide a proof that a microorganism which belongs to genus Erwinia is compatible with one which belongs to genus Brevibacterium or Corynebacterium in a process for preparing 2-keto-L-gulonic acid which has achieved a better result than the prior art in obtaining the intended product.

According to the present invention, there is provided, in the process for preparing 2-keto-L-gulonic acid or a salt thereof from D-glucose by cultivation a mixed culture of a first microorganism (1) capable of producing 2,5-diketo-D-gluconic acid from D-glucose and a second microorganism (2) capable of converting 2,5-diketo-D-gluconic acid into 2-keto-L-gulonic acid in a medium containing D-glucose wherein both of said microorganisms are present together, a process characterized in that said first microorganisms belongs to the genus Erwinia and said second microorganism belongs to the genus Brevibacterium or Corynebacterium. The incubation of the microorganisms in a medium containing D-glucose is used in the disclosed process. By-production of 2-keto-D-gluconic acid, the undesired isomer of the intended product is effectively prevented by employing the mixed culturing because of the co-existence of both microorganisms in the medium during at least part of the entire cultivation. Namely, 2-keto-D-gluconic acid produced by the second microorganism is utilized by the first microorganism to produce 2,5-diketo-D-gluconic acid which is subsequently converted into 2-keto-L-gulonic acid by the second microorganism.

In performing the process of the present invention, the known conventional conditions employed in "mixed culture" and in its subsequent steps as disclosed in, for instance, U.S. Pat. No. 3,998,697 may likewise be applied with some obvious modification and adjustment.

The "mixed culture" involves the following three processes (a), (b) and (c); (a) a process wherein both kinds of microorganisms are simultaneously inoculated in the medium at the initiation of the cultivation, (b) a process wherein the medium is inoculated with the first microorganism and, the second microorganism is inoculated in the medium after a period of incubation and (c) a process wherein the both microorganisms are inoculated separately in the respective media and then either one of the both is added to the other broth all at once, portionwise or continously after some period of incubation, followed by another period of incubation.

In order to allow the microorganisms to produce the end product, 2-keto-L-gulonic acid most effectively, a ratio of inoculum sizes of both microorganisms and timing of inoculation should be determined in consideration of growth rates of both microorganisms, an activity of the first microorganism in 2,5-diketo-D-gluconic acid production, an activity of the second microorganism in converting 2,5-diketo-D-gluconic acid into 2-keto-L-gulonic acid, and the property of the media, and these considerations should not be construed to be limited to those described in the working example of the present invention.

The first and second microorganisms (hereinafter, will be referred to as strain (I) and strain (II)) which can be employed in embodying the present invention are listed for exemplification in Tables 1 and 2 below, respectively.

TABLE 1

| 2,5-diketo-D-gluconic acid-producing microorganism (strain (I)) | FERM-P | ATCC |
|---|---|---|
| Erwinia citreus | 5449 | 31623 |
| Erwinia punctata | 5452 | 31626 |
| Erwinia punctata var. | 5450 | 31624 |
| Erwinia punctata var. | 5451 | 31625 |
| Erwinia punctata var. | 5453 | 31627 |
| Erwinia punctata var. | 5453 | 31627 |
| Erwinia terreus | 5454 | 31628 |
| Erwinia terreus var. | 5455 | 31629 |
| Erwinia terreus var. | 5456 | 31630 |
| Erwinia terreus var. | 5457 | 31631 |

TABLE 2

| 2-keto-L-gulonic acid-producing microorganism (strain (II)) | FERM-P | ATCC |
|---|---|---|
| Brevibacterium ketosoreductum nov. sp. | 1905 | 21914 |
| Brevibacterium nov. sp. | 2686 | 31083 |
| Brevibacterium sp. | 2685 | 31082 |
| Brevibacterium testaceum IFO 12675 | — | — |
| Corynebacterium sp. | 2687 | 31081 |
| Corynebacterium sp. | 2771 | 31089 |
| Corynebacterium sp. | 2769 | 31088 |
| Corynebacterium sp. | 2770 | 31090 |

These microorganisms are deposited with the Fermentation Research Institute, Yatabe, Japan as FERM-Ps and with the American Type culture Collection, Maryland, U.S.A. as ATCCs by the present inventors, and samples of these are available from those depositories under the provision of the Budapest Treaty.

Detailed taxonomical descriptions of these are given in either of European Patent Publication No. 0 046 284, U.S Pat. Nos. 3,922,194, 3,959,076 and 3,963,574. *Brevibacterium testaceum* which is given IFO number 12675 is available from the Institute of Fermentation, Osaka, Japan and is described in Bergey's Manual of Determinative Bacteriology 8th Ed..

Any mutant derived from the above-described strains (I) and (II) by mutating the strains by irradiating ultraviolet ray or X-ray, or by treating them with chemicals, may similarly be employed for embodying the present invention more efficiently.

In the present invention, no particular restriction should be imposed on the composition of the nutrient medium used for the cultivation of the strains (I) and (II), though it should desirably contain carbon sources, nitrogen sources, other inorganic salts, and trace amounts of other factors which are assimilable by the strains. Although D-glucose, the starting substrate material, is mainly used as the carbon source, any conventionally employed carbon sources such as sucrose, glycerol, molasses and the like can also be used. As the nitrogen sources, there may be exemplified as corn steep liquor, peptone, meat extract, yeast, yeast extract, soy bean meal, wheat gluten, any nitrogen compounds such as urea and the like.

As the inorganic salts, calcium salts, magnesium salts, potassium salts, zinc salts, iron salts and other metals essential for growth can be employed. Furthermore, if necessary, any factors for promoting the growth of the microorganism and its production of the end product may also be added to the medium. The ratio of mixing these various nutrients and factors varies with the characters of the employed strains, the previously-described manner of inoculation, the amount of substrate D-glucose to be used, and the attendant conditions, and can therefore be suitably selected and determined in accordance with these conditions of the respective cases.

Although the concentration of the substrate D-glucose in the fermentation medium may vary with the species of the strain, a concentration of 10–300 g/l is usually applied.

Although the cultivating conditions may vary with the species of the strain, the composition of the medium, the previously-described manner of inoculations of both strains, the ratio of inoculum sizes of both strains, the timing of the inoculation and other attendant conditions, it is usually desirable to keep the cultivation temperature at 20°–35° C. and to keep the pH of the medium to 4–9. For this purpose, a suitable acidic or basic substance may be added to the medium at a suitable time during the cultivation, or alternatively, a buffering agent may initially be included in the starting medium in a suitable amount. The cultivation time may usually extend to 10–100 hours.

The 2,5-diketo-D-gluconic acid produced by cultivating the strain (I) is directly converted into 2-keto-L-gulonic acid by the strain (II) without being isolated from the medium. The undesired 2-keto-D-gluconic acid produced by the strain (II) is converted into 2,5-diketo-D-gluconic acid by the strain (I) which is again converted into 2-keto-L-gulonic acid by the strain (II).

The 2-keto-L-gulonic acid thus produced and accumulated in the culture medium can be isolated from the medium and purified in a conventional manner.

The identification of the 2-keto-L-gulonic acid obtained in the process of the present invention can be performed by elemental analysis and measurement of physio-chemical properties such as melting point, infrared absorption spectrum, optical rotation and the like.

As described above, the present invention has advantages in the production of 2-keto-L-gulonic acid in that (a) first, it can produce 2-keto-L-gulonic acid from D-glucose in one step process, (b) second, it can eliminate the need for separating an intermediate, and (c) third, no concomittant production of the undesired isomer, and the advantages will bring about prominent results in commercial-scale application.

DESCRIPTION OF THE PREFERRED EMBODIMENT

In the following description, the present invention will be elucidated in more detail by way of example, wherein percentages in the composition represent weight by volume percentages.

EXAMPLE 1

(1) Production of 2,5-diketo-D-gluconic acid by the strain (I)

*Erwinia punctata* FERM-P 5452 was employed as the microorganism in this example.

(i) Seed medium:
An aqueous solution containing;
D-glucose: 1.0%,

Corn steep liquor (CSL): 5.0%, Potassium primary phosphate (KH$_2$PO$_4$): 0.1%, Magnesium sulfate (MgSO$_4$.7H$_2$O): 0.02%, and Calcium Carbonate (CaCO$_3$): 0.5%.

was adjusted to pH 6.8-7.0 with 10% NaOH solution and each 50 ml portion thereof was poured into a 500 ml conical flask which was then sterilized at 120° C. for 20 minutes.

(ii) Seed culture:

The seed medium in the above flask was inoculated with one loopful of FERM-P 5452 (Table 3) and incubated at 28° C. for 8-11 hours under agitation (71 mm in amplitude, 270 r.p.m.). When the optical density (O.D.) of the culture became about 8, the seed culture was terminated (end point).

(iii) Fermentation medium:

An aqueous solution containing:
D-glucose: 20%,
CSL: 3%,
KH$_2$PO$_4$: 0.1%,
CaCO$_3$: 6.3%, and
Polypropylene glycol 2000 (P-2000): 0.01%.

was adjusted to pH 6.8-7.0 as described above and sterilized at 120° C. for 20 minutes. Each 455 ml portion thereof was poured into a 1 liter sterilized fermenter and inoculated with 45 ml of the above seed culture.

(iv) Condition of fermentation:
Temperature: 28° C.,
Agitation: 1740 r.p.m.,
Aeration: 600 Nml/min.,
Time: 17-31 hours.

(v) Analysis:

The products in the fermentation broth were analyzed by ascending paper chromatography of the details listed below and were quantitatively determined by densitometry.

(a) Carrier: Toyo Roshi No. 50, available from Toyo Roshi K.K.

(b) Developing solvent:Phenol:Formic acid:Water =75:4:25

(c) Color development: Spraying AHF solution (prepared by dissolving 0.93 g of aniline and 1.66 g of phthalic acid in 100 ml of water saturated n-butanol) and heating at 105° C. for 2 minutes.

In addition to this, a thin-layer chromatography on a carrier "TLC alumisheet cellulose" (available from Merck A. G.) was paralelly performed with the above-described developing solvent and color development conditions. In this case, however, the quantitative determination was made by a comparison with that of an authentic sample.

(vi) End point:

The fermentation was terminated when a pink spot of 2-keto-D-gluconic acid disappeared from the above-described thin-layer chromatogram.

(2) Preparation of 2,5-diketo-D-gluconic acid solutions:

In order to confirm the advantages of the mixed culture, the following three kinds of 2,5-diketo-D-gluconic acid-containing solutions were prepared.

(i) The 2,5-diketo-D-gluconic acid containing fermentation broth prepared by the strain (I) under the conditions (1) (iv) above, diluted to about fourfold dilution with sterilized water (containing in $10^8$-$10^{10}$ viable cells of the strain (I)/ml).

(ii) (i), centrifuged and sterilized by filtration (control 1).

(iii) An aqueous solution containing 5% of calcium 2,5-diketo-D-gluconate, sterilized by filtration (control 2).

(3) Production of 2-keto-L-gulonic acid from 2,5-diketo-D-gluconic acid by the strain (II)

(i) Seed medium:

An aqueous solution containing:
D-glucose: 1.0%,
Bacto Yeast Extract (Difco): 0.5%,
Bacto Peptone (Difco): 0.5%,
KH$_2$PO$_4$: 0.1%, and
MgSO$_4$.7H$_2$O: 0.02%.

was adjusted to pH 7.0-7.2 with 10% of NaOH and each 50 ml thereof was poured into a 500 ml conical flask which was then sterilized at 115° C. for 15 minutes.

(ii) Seed culture:

Each of the seed medium (i) in the above flask was inoculated with each one loopful of the strains (II) listed in Table 2 and incubated at 28° C. for 16-24 hours under agitation (71 mm in amplitude, 270 r.p.m.).

(iii) Fermentation medium:

An aqueous solution containing:
D-glucose: 1.0%,
CSL: 3.0%,
KH$_2$PO$_4$: 0.1%, and
MgSO$_4$.7H$_2$O: 0.02%.

was adjusted to pH 7.0-7.2 with 10% NaOH and each 50 ml portion thereof was poured into a 500 ml conical flask which was then sterilized at 115° C. for 20 minutes.

(iv) Fermentation:

Each 5 ml of the seed culture of the strain (II) was inoculated in each of the above fermentation media in the flask. The previously prepared 2,5-diketo-D-gluconic acid solutions (2), (i) (ii) and (iii) were individually added to the fermentation medium, at the beginning of the fermentation or 16 hours after the beginning of the fermentation (agitation: 71 mm in amplitude, 270 r.p.m. at 28° C.) to give a 2,5-diketo-D-gluconic acid concentration of 2,5%. The 2,5-diketo-D-gluconic acid fermentation broth (i) contains viable cells of the strain (I). Thereafter, the cultivations were continued for another 48 hours, respectively, (v) Quantitative analysis:

Gas-liquid chromatography (Column: SE 52 (5%); Sample; Trimethylsilylated; Temperature; 160°-210° C.; Carrier gas; Helium).

The results of the fermentation were summarized in Table 3 and 4.

As shown in these tables, no concomittant production of 2-keto-D-gluconic aicd was observed in the case of the mixed culture of the strains (I) and (II), whereas the production of 2-keto-D-gluconic acid was observed with the accumulation of the 2-keto-L-gulonic acid in both cases of the pure culture of the strain (II) in the control groups.

TABLE 3

| 2-Keto-L-gulonic acid producing microorganism strain (II) | Time when 25DKG was added (hours after the beginning of the cultivation) | Accumulation of 2KLG or 2KDG, mg/ml | | | | | |
|---|---|---|---|---|---|---|---|
| | | Mixed culture | | Pure culture | | | |
| | | FERM-P 5452 fermentation broth (no sterilization) | | FERM-P 5452 fermentation broth (sterilized by filtration) | | Aqueous soln. of Ca 25DKDG (sterilized by filtration) | |
| | | 2KLG, mg/ml | 2KDG, mg/ml | 2KLG, mg/ml | 2KDG, mg/ml | 2KLG, mg/ml | 2KDG, mg/ml |
| *Brevibacterium ketoso-reductum* nov. sp. FERM-P 1905 | 0 | 0.41 | 0 | 0.73 | 0.35 | 0.63 | 0.25 |
| | 16 | 1.46 | 0 | 1.85 | 0.73 | 1.22 | 0.74 |
| Brevibacterium nov. sp. FERM-P 2686 | 0 | 0.65 | 0 | 1.35 | 0.15 | 0.78 | 0.20 |
| | 16 | 2.43 | 0 | 3.05 | 0.35 | 2.15 | 0.25 |
| Brevibacterium sp. FERM-P 2685 | 0 | 0.47 | 0 | 0.45 | 0.21 | 0.18 | 0.08 |
| | 16 | 1.30 | 0 | 1.95 | 0.68 | 1.75 | 0.63 |
| *Brevibacterium testaceum* IFO 12675 | 0 | 0.13 | 0 | 0.08 | 0.07 | 0.07 | 0.07 |
| | 16 | 0.15 | 0 | 0.12 | 0.08 | 0.10 | 0.05 |

25DKG: 2,5-diketo-D-gluconic acid or 2,5-diketo-D-gluconate
2KLG: 2-keto-L-gulonic acid
2KDG: 2-keto-D-gluconic acid

TABLE 4

| 2-Keto-L-gulonic acid-producing microorganism strain (II) | Time when 25DKG was added (hours after the beginning of the cultivation) | Accumulation of 2KLG or 2KDG, mg/ml | | | | | |
|---|---|---|---|---|---|---|---|
| | | Mixed culture | | Pure culture | | | |
| | | FERM-P 5452 fermentation broth (no sterilization) | | FERM-P 5452 fermentation broth (sterilized by filtration) | | Aqueous soln. of Ca 25DKDG (sterilized by filtration) | |
| | | 2KLG, mg/ml | 2KDG, mg/ml | 2KLG, mg/ml | 2KDG, mg/ml | 2KLG, mg/ml | 2KDG, mg/ml |
| Corynebacterium sp. FERM-P 2687 | 0 | 1.60 | 0 | 0.35 | 0.11 | 0.25 | 0.47 |
| | 16 | 1.85 | 0 | 0.50 | 0.83 | 0.73 | 0.86 |
| Corynebacterium sp. FERM-P 2771 | 0 | 0.89 | 0 | 0.65 | 0.23 | 0.58 | 0.17 |
| | 16 | 1.36 | 0 | 1.27 | 0.47 | 1.03 | 0.25 |
| Corynebacterium sp. FERM-P 2769 | 0 | 0.98 | 0 | 0.84 | 0.05 | 0.97 | 0.07 |
| | 16 | 2.65 | 0 | 2.45 | 0.10 | 2.86 | 0.79 |
| Corynebacterium sp. FERM-P 2770 | 0 | 1.46 | 0 | 1.23 | 0.19 | 1.06 | 0.31 |
| | 16 | 4.68 | 0 | 4.51 | 1.86 | 4.03 | 1.43 |

25DKG: 2,5-diketo-D-gluconic acid or 2,5-diketo-D-gluconate
2KLG: 2-keto-L-gulonic acid
2KDG: 2-keto-D-gluconic acid

EXAMPLE 2

In this example, *Erwinia punctata* FERM-P 5452 was used as the strain (I) and *Brevibacterium ketosoreductum* FERM-P 1905 and Corynebacterium sp. FERM-P 2770 were used as the strain (II), respectively.

Seed cultures of the strains (I) and (II) were prepared in the same manner as those described in Example 1. As another preparation, a fermentation medium was prepared by adjusting the pH of an aqueous solution containing 3% of D-glucose, 3% of CSL, 0.2% of Bacto Yeast Extract (Difco), 0.1% of $KH_2PO_4$, 0.02% of $MgSO_4.7H_2O$ and 1.0% of $CaCO_3$ to 7.0–7.2 with 10% NaOH solution and each 50 ml portion thereof was poured into a 500 ml conical flask which was then sterilized at 115° C. for 20 minutes. Each of the fermentation media was inoculated with each 1.0 ml of the seed culture of the strain (I) and with each 4.0 ml of either of the seed cultures of the strain (II) and cultivated under agitation (71 mm in amplitude, 270 r.p.m.,) at 28° C. for 48 hours.

After cultivation, the cultured broths were analyzed in the same manner as described in Example 1 and the results are summarized in Table 5. As apparent from Table 5, although an accumulation of 2-keto-L-gulonic acid was observed, no accumulation of 2-keto-D-gluconic acid was observed.

TABLE 5

| 2-Keto-L-gulonic acid producing microorganism strain (II) | Accumulation of 2-keto-L-gulonic acid, mg/ml |
|---|---|
| *Brevibacterium ketosoreductum* nov. sp. FERM-P 1905 | 0.37 |
| Corynebacterium sp. FERM-P 2770 | 1.28 |

What is claimed is:

1. A process for preparing 2-keto-L-gulonic acid from D-glucose, comprising: cultivating in a nutrient medium containing D-glucose a mixed culture of a first microorganism selected from the group consisting of the species *Erwinia citreus, Erwinia punctata, Erwinia terreus* and mutants thereof capable of converting D-glucose into 2,5-diketo-D-gluconic acid and a second microorganism belonging to the genus Brevibacterium or Corynebacterium capable of converting 2,5-diketo-D-gluconic acid into 2-keto-L-gulonic acid wherein said first and second microorganisms are incubated in the medium in such a manner that both microorganisms coexist and grow together therein during at least the latter part of the cultivation.

2. A process as claimed in claim 1, wherein said first and second microorganisms, (1) and (2), are incubated in the medium in such a manner that both microorganisms coexist and grow together therein during at least a latter part of the cultivation.

3. A process as claimed in claim 2, wherein the first microorganism belongs to genus Erwinia and the second microorganism belongs to genus Brevibacterium.

4. A process as claimed in claim 3, wherein the first microorganism belongs to species which includes *Erwinia citreus* ATCC 31623.

5. A process as claimed in claim 3, wherein the second microorganism belongs to species which includes *Brevibacterium ketosoreductum* nov. sp. ATCC 21914.

6. A process as claimed in claim 3, wherein the second microorganism belongs to the species which includes Brevibacterium nov. sp. ATCC 31083.

7. A process as claimed in claim 3, wherein the second microorganism belongs to species which includes Brevibacterium sp. ATCC 31082.

8. A process as claimed in claim 3, wherein the second microorganism belongs to the species which includes *Brevibacterium testaceum* IFO 12675.

9. A process as claimed in claim 3, wherein said first microorganism is selected from the group consisting of *Erwinia punctata* ATCC 31626, *Erwinia punctata* var. ATCC 31624, *Erwinia punctata* var. ATCC 31625 and *Erwinia punctata* var. ATCC 31627.

10. A process as claimed in claim 3, wherein said first microorganism is selected from the group consisting of *Erwinia terreus*, ATCC 31628, *Erwinia terreus* var. ATCC 31629, *Erwinia terreus* var. ATCC 31630 and *Erwinia terreus* var. ATCC 31631.

11. A process as claimed in claim 2, wherein the first microorganism belongs to genus Erwinia and the second microorganism belongs to genus Corynebacterium.

12. A process as claimed in claim 11, wherein the second microorganism belongs to species which includes Corynebacterium sp. ATCC 31081.

13. A process as claimed in claim 11, wherein the second microorganism belongs to species which includes Corynebacterium sp. ATCC 31089.

14. A process as claimed in claim 11, wherein the second microorganism belongs to species which includes Corynebacterium sp. ATCC 31088.

15. A process as claimed in claim 11, wherein the second microorganism belongs to species which includes Corynebacterium sp. ATCC 31090.

16. A process as claimed in claim 11, wherein the first microorganism belongs to species which includes *Erwinia citreus* ATCC 31623.

17. A process as claimed in claim 11, wherein the first microorganism is selected from the group consisting of *Erwinia terreus*, ATCC 31628, *Erwinia terreus* var. ATCC 31629, *Erwinia terreus* var. ATCC 31630 and *Erwinia terreus* var. ATCC 31631.

18. A process as claimed in claim 11, wherein said first microorganism is selected from the group consisting of *Erwinia punctata* ATCC 31626, *Erwinia punctata* var. ATCC 31624, *Erwinia punctata* var. ATCC 31625 and *Erwinia punctata* var. ATCC 31627.

19. A process for preparing 2-keto-L-gulonic acid from D-glucose, comprising: cultivating in a nutrient medium containing D-glucose a mixed culture of a first microorganism selected from the group consisting of the species *Erwinia citreus, Erwinia punctata, Erwinia terreus* and mutants thereof capable of converting D-glucose into 2,5-diketo-D-gluconic acid and capable of converting 2-keto-D-gluconic acid into 2,5-diketo-D-gluconic acid and a second microorganism belonging to the genus Brevibacterium or Corynebacterium capable of converting 2,5-diketo-D-gluconic acid into 2-keto-L-gulonic acid wherein said first and second microorganisms are incubated in the medium in such a manner that both microorganisms coexist and grow together therein during at least a latter part of the cultivation and 2-keto-D-gluconic acid produced as a by-product by said second microorganism is converted into 2,5-diketo-D-gluconic acid by said first microganism.

20. A process as claimed in claim 19, wherein said first microorganism is selected from the group consisting of *Erwinia citreus* ATCC 31623, *Erwinia punctata* ATCC 31626, *Erwinia punctata* var. ATCC 31624, *Erwinia punctata* var. ATCC 31625, *Erwinia punctata* var. ATCC 31627, *Erwinia terreus* ATCC 31628, *Erwinia terreus* var. ATCC 31629, *Erwinia terreus* var. ATCC 31630, *Erwinia terreus* var. ATCC 31631 and mutants thereof and said second microorganism is selected from the group consisting of *Brevibacterium ketosoreductum* nov. sp. ATCC 21914, Brevibacterium nov. sp. ATCC 31083, Brevibacterium sp. ATCC 31082, *Brevibacterium testaceum* IFO 12675, Corynebacterium sp. ATCC 31081, Corynebacterium sp. ATCC 31089, Corynebacterium sp. ATCC 31088, Corynebacterium sp. ATCC 31090 and mutants thereof.

* * * * *